United States Patent
Adachi et al.

(10) Patent No.: US 8,901,543 B2
(45) Date of Patent: Dec. 2, 2014

(54) ORGANIC SEMICONDUCTOR DEVICE AND ITS PRODUCTION METHOD, AND COMPOUND

(75) Inventors: Chihaya Adachi, Fukuoka (JP); Takuma Yasuda, Fukuoka (JP); Yang Yu Seok, Fukuoka (JP); Hayato Kakizoe, Fukuoka (JP); Hiroyuki Mieno, Fukuoka (JP)

(73) Assignee: Kyushu University National University Corporation, Fukuoka (JP)

( * ) Notice: Subject to any disclaimer, the term of this patent is extended or adjusted under 35 U.S.C. 154(b) by 168 days.

(21) Appl. No.: 13/566,290

(22) Filed: Aug. 3, 2012

(65) Prior Publication Data

US 2013/0207081 A1 Aug. 15, 2013

(30) Foreign Application Priority Data

Feb. 15, 2012 (JP) ................................. 2012-030705

(51) Int. Cl.
*H01L 35/24* (2006.01)
(52) U.S. Cl.
USPC ..................................... 257/40; 257/E51.001
(58) Field of Classification Search
USPC ............................................ 257/40, E51.001
See application file for complete search history.

(56) References Cited

FOREIGN PATENT DOCUMENTS

| | | |
|---|---|---|
| JP | 2003073382 A | 3/2003 |
| JP | 2005076030 A | 3/2005 |
| JP | 2006089413 A | 4/2006 |
| JP | 2008007497 A | 1/2008 |

OTHER PUBLICATIONS

Zhang et al, "Synthesis, self-assembly, and solution-processed nanoribbon field-effect transistor of a fused-nine-ring thienoacene," The Royal Society of Chemistry, Chem. Commun., 2010, 46, pp. 2841-2843.*

* cited by examiner

*Primary Examiner* — Anthony Ho
(74) *Attorney, Agent, or Firm* — Browdy and Neimark, PLLC (57) ABSTRACT

An organic semiconductor device which has an organic semiconductor layer formed by crystallizing a compound represented by the following formula (1) from a solution of the compound:

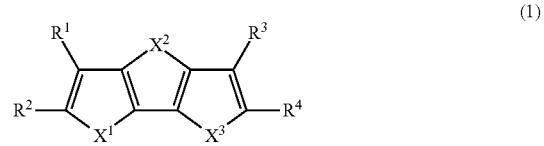

(1)

wherein $X^1$, $X^2$ and $X^3$ represent O, S, Se or Te; at least one of $R^1$, $R^2$, $R^3$ and $R^4$ represents a group that has both an aromatic ring to form a π-conjugated system with the skeleton to which it bonds, and a chainlike structure in which the number of the carbon atoms constituting the main chain is from 4 to 20, and the remaining ones represent a hydrogen atom or a substituent.

23 Claims, 1 Drawing Sheet

ORGANIC SEMICONDUCTOR DEVICE AND ITS PRODUCTION METHOD, AND COMPOUND

CROSS-REFERENCE TO RELATED APPLICATIONS

The present application claims the benefit of priority from Japanese Patent Application No. 2012-30705, filed on Feb. 15, 2012, the contents of which are herein incorporated by reference in their entirety.

BACKGROUND OF THE INVENTION

1. Field of the Invention

The present invention relates to an organic semiconductor device such as a field-effect transistor or the like, and to a method for producing the device. The invention also relates to a compound for use for the organic semiconductor layer of an organic semiconductor device.

2. Description of the Related Art

Some types of organic semiconductor layers formed by the use of a chainlike compound that contains multiple thiophene structure in the molecule thereof are known to have a high carrier mobility. For example, it has been reported that some types of organic semiconductor layers formed by the use of an oligothiophene derivative or a chainlike compound that contains a thieno[3,2-b]thiophene structure or a dithieno[3,2-b:2',3'-d]thiophene structure have a high carrier mobility (for example, see Patent References 1 to 4). Use of the organic semiconductor layer containing such a compound as an organic semiconductor layer to constitute an organic semiconductor device such as a field-effect transistor or the like has been proposed.

CITATION LIST

Patent References

[Patent Reference 1] JP-A 2008-7497
[Patent Reference 2] JP-A 2006-89413
[Patent Reference 3] JP-A 2005-76030
[Patent Reference 4] JP-A 2003-73382

SUMMARY OF THE INVENTION

As in the above, various investigations have heretofore been made of chainlike compounds that contain multiple thiophene structures in the molecule thereof, and some proposals have been made relating to the application of those compounds to field-effect transistors. However, it could not be said that exhaustive studies relating to all chainlike compounds that contain multiple thiophene structures in the molecule thereof could have been entirely made. In particular, regarding the use of compounds having a dithieno[3,2-b:2',3'-d]thiophene structure as organic semiconductor materials, the usefulness of only a part of those compounds has merely been confirmed. In addition, any definite relationship between the chemical structure of chainlike compounds containing multiple thiophene structures in the molecule thereof and the usefulness of those compounds as organic semiconductor materials (especially in point of the carrier mobility thereof) has not as yet been clarified, and in fact, it is still difficult to accurately forecast the usefulness of compounds as organic semiconductor materials based on the chemical structure thereof. On the other hand, many chainlike compounds containing multiple thiophene structures in the molecule thereof that have heretofore been proposed in the art are difficult to dissolve in solvent. In forming an organic semiconductor layer by the use of such a compound, used is a vacuum evaporation method, but the method is problematic in that it requires a large-scale production apparatus and the production cost is high. Taking these matters into consideration, the present inventors have promoted various investigations mainly for the purpose of providing an organic semiconductor device that has an organic semiconductor layer having a high carrier mobility. In addition, the inventors have further studied for the purpose of inexpensively producing an organic semiconductor device having an organic semiconductor layer that shows a high carrier mobility, not requiring any large-scale production apparatus.

The present inventors have assiduously studied for the purpose of attaining the above-mentioned object and, as a result, have found that when an organic semiconductor layer is formed by the use of a compound having a specific structure according to a specific production method, then an organic semiconductor layer having a high carrier mobility can be produced in a simplified manner. In addition, the inventors have found that the organic semiconductor layer that contains a novel compound having a more limited structure can exhibit a higher carrier mobility irrespective of the production method for the layer. Based on these findings, the inventors have reached the present invention described below as a means for solving the above-mentioned problems.

[1] An organic semiconductor device which has an organic semiconductor layer formed by crystallizing a compound represented by the following formula (1) from a solution of the compound:

wherein $X^1$, $X^2$ and $X^3$ each independently represent an oxygen atom, a sulfur atom, a selenium atom or a tellurium atom; at least one of $R^1$, $R^2$, $R^3$ and $R^1$ represents a group that has both an aromatic ring to form a π-conjugated system with the skeleton to which it bonds, and a chainlike structure in which the number of the carbon atoms constituting the main chain is from 4 to 20, and the remaining ones each independently represent a hydrogen atom or a substituent; $R^1$ and $R^2$ may bond to each other to form a cyclic structure, and $R^3$ and $R^4$ may bond to each other to form a cyclic structure.

[2] The organic semiconductor device according to [1], wherein the organic semiconductor layer is formed by crystallizing a compound represented by the following formula (2) from a solution of the compound:

wherein $X^1$, $X^2$ and $X^3$ each independently represent an oxygen atom, a sulfur atom, a selenium atom or a tellurium atom; $R^1$ and $R^3$ each independently represent a hydrogen atom or a substituent; at least one of $R^{11}$, $R^{12}$, $R^{13}$, $R^{14}$, $R^{15}$, $R^{21}$, $R^{22}$, $R^{23}$, $R^{24}$ and $R^{25}$ represents a group having a chainlike structure of which the number of the atoms of the main chain is from 4 to 20, and the remaining ones each independently represent a hydrogen atom or a substituent.

[3] The organic semiconductor device according to [2], wherein the group having a chainlike structure in which the number of the carbon atoms constituting the main chain is from 4 to 20 has a structure represented by the following formula (5):

wherein Ar represents an aromatic linking group; and m indicates an integer of from 4 to 20.

[4] The organic semiconductor device according to [2], wherein the group having a chainlike structure in which the number of the carbon atoms constituting the main chain is from 4 to 20 has a structure represented by the following formula (6):

wherein Ar represents an aromatic linking group; and m indicates an integer of from 4 to 20.

[5] The organic semiconductor device according to any one of [2] to [4], wherein at least one of $R^{13}$ and $R^{23}$ is a group having a chainlike structure in which the number of the carbon atoms constituting the main chain is from 4 to 20.

[6] The organic semiconductor device according to any one of [2] to [4], wherein at least one of $R^{13}$ and $R^{23}$ is a group having a chainlike structure in which the number of the carbon atoms constituting the main chain is from 8 to 20.

[7] The organic semiconductor device according to any one of [1] to [6], wherein $X^1$, $X^2$ and $X^3$ are the same atoms.

[8] The organic semiconductor device according to [7], wherein $X^1$, $X^2$ and $X^3$ are sulfur atoms.

[9] The organic semiconductor device according to any one of [1] to [6], wherein $X^1$ and $X^3$ are sulfur atoms and $X^2$ is a selenium atom or a tellurium atom.

[10] The organic semiconductor device according to any one of [1] to [9], which is a field-effect transistor.

[11] A method for producing an organic semiconductor device, which comprises forming an organic semiconductor layer by crystallizing a compound represented by the above formula (1) from a solution of the compound.

[12] The method for producing an organic semiconductor device according to [11], wherein the organic semiconductor layer is formed by crystallizing a compound represented by the above formula (2) from a solution of the compound.

[13] The method for producing an organic semiconductor device according to [11] or [12], wherein the solution is a solution in a halogen solvent.

[14] The method for producing an organic semiconductor device according to anyone of [11] to [13], wherein the solvent is an aromatic solvent.

[15] A compound having a structure represented by the above formula (2) from a solution of the compound.

[16] A compound according to [15], wherein the group having a chainlike structure in which the number of the carbon atoms constituting the main chain is from 4 to 20 has a structure represented by the following formula (5):

wherein Ar represents an aromatic linking group; and m indicates an integer of from 4 to 20.

[17] The compound according to [15], wherein the group having a chainlike structure in which the number of the carbon atoms constituting the main chain is from 4 to 20 has a structure represented by the following formula (6):

wherein Ar represents an aromatic linking group; and m indicates an integer of from 4 to 20.

[18] The compound according to any one of [15] to [17], wherein at least one of $R^{13}$ and $R^{23}$ is a group having a chainlike structure in which the number of the carbon atoms constituting the main chain is from 4 to 20.

[19] The compound according to any one of [15] to [17], wherein at least one of $R^{13}$ and $R^{23}$ is a group having a chainlike structure in which the number of the carbon atoms constituting the main chain is from 8 to 20.

[20] The compound according to any one of [15] to [19], wherein $X^1$, $X^2$ and $X^3$ are the same atoms.

[21] The compound according to [20], wherein $X^1$, $X^2$ and $X^3$ are sulfur atoms.

[22] The compound according to any one of [15] to [19], wherein $X^1$ and $X^3$ are sulfur atoms and $X^2$ is a selenium atom or a tellurium atom.

[23] An organic semiconductor device comprising the compound of any one of [15] to [22].

The organic semiconductor device of the invention, which has an organic semiconductor layer formed by crystallizing a compound represented by the formula (1) from a solution of the compound, has a high carrier mobility and has a large on/off ratio. In addition, the organic semiconductor device of the invention, which has an organic semiconductor layer containing a compound represented by the formula (2), has a relatively high carrier mobility irrespective of the production method for the device, and has a large on/off ratio.

MODE FOR CARRYING OUT THE INVENTION

The contents of the invention are described in detail hereinunder. The description of the constitutive elements of the invention given hereinunder is for some typical embodiments and specific examples of the invention; however, the invention should not be limited to such embodiments and specific examples. In this description, the numerical range expressed by the wording "a number to another number" means the range that falls between the former number indicating the lower limit of the range and the latter number indicating the upper limit thereof.

[Compound Represented by Formula (1)]

For the organic semiconductor layer of the organic semiconductor device of the invention, a compound represented by the following formula (1) is used.

In the formula (1), $X^1$, $X^2$ and $X^3$ each independently represent an oxygen atom, a sulfur atom, a selenium atom or a tellurium atom. Employing a selenium atom or a tellurium atom, the organic semiconductor layer is expected to show a higher carrier mobility. All $X^1$, $X^2$ and $X^3$ may be the same, or a part or all of these may differ. The case where all $X^1$, $X^2$ and $X^3$ are the same has the advantage that the production of the compound is easy. For example, there is mentioned an example where all $X^1$, $X^2$ and $X^3$ are sulfur atoms. On the other hand, an embodiment where $X^1$ and $X^3$ are the same while $X^2$ differs from them is also preferred; and for example, there are mentioned a case where $X^1$ and $X^3$ are sulfur atoms and $X^2$ is a selenium atom, and a case where $X^1$ and $X^3$ are sulfur atoms and $X^2$ is a tellurium atom.

In the formula (1), at least one of $R^1$, $R^2$, $R^3$ and $R^4$ represents a group that has both an aromatic ring to form a π-conjugated system with the skeleton to which it bonds, and a chainlike structure in which the number of the carbon atoms constituting the main chain is from 4 to 20, and the remaining ones each independently represent a hydrogen atom or a substituent. In the "group that has both an aromatic ring to form a π-conjugated system with the skeleton to which it bonds, and a chainlike structure in which the number of the carbon atoms constituting the main chain is from 4 to 20", the "skeleton to which it bonds" is a skeleton represented by the following formula (3):

(3)

The aromatic ring to form a π-conjugated system with the above-mentioned skeleton includes those in which the atoms to constitute the ring skeleton are carbon atoms alone and those in which the atoms include hetero atoms. For example, there are mentioned a benzene ring, a naphthalene ring, an anthracene ring, a phenanthrene ring, a furan ring, a thiophene ring. Of those, for example, a benzene ring, a naphthalene ring, a furan ring or a thiophene ring may be selected, and further a benzene ring or a thiophene ring may be selected. The aromatic ring may be directly bonded to the skeleton represented by the formula (3), or may be bonded thereto via a linking group having a π-conjugated system. The linking group having a π-conjugated system includes a linking group represented by the following formula (4):

(4)

In the formula (4), $R^{31}$ and $R^{32}$ each independently represent a hydrogen atom or a substituent. n indicates an integer of from 1 to 10. One example of the linking group represented by the formula (4) is a linking group having the following structure.

—CH═CH—

The chainlike structure in the "group that has both an aromatic ring to form a π-conjugated system with the skeleton to which it bonds, and a chainlike structure in which the number of the carbon atoms constituting the main chain is from 4 to 20" is meant to indicate a structure in which the number of the carbon atoms to constitute the main chain is from 4 to 20. Preferably, the number of the carbon atoms to constitute the main chain is from 8 to 20. The "number of the carbon atoms to constitute the main chain" means the number of the carbon atoms to constitute the longest chain (main chain) in the chainlike structure, and the main chain may contain any other atom than the carbon atoms (for example, hetero atom such as oxygen atom, sulfur atom). For example, there are mentioned a substituted or unsubstituted linear alkyl group, a substituted or unsubstituted linear alkenyl group, a substituted or unsubstituted linear alkenyl group, and those derived from these groups by substituting at least one carbon atom to constitute the main chain therein with a hetero atom such as an oxygen atom, a sulfur atom or the like. Preferred are a substituted or unsubstituted n-alkyl group, and a substituted or unsubstituted n-alkoxy group; and for example, there is mentioned an unsubstituted n-alkyl group having from 4 to 20 carbon atoms. Concretely, there are mentioned an n-hexyl group, an n-octyl group, an n-decyl group, an n-dodecyl group, a tetradecyl group, an n-hexyloxy group, an n-octyloxy group, an n-decyloxy group, an n-dodecyloxy group, a tetradecyloxy group.

Preferably, the number of the aromatic rings to constitute the "group that has both an aromatic ring to form a π-conjugated system with the skeleton to which it bonds, and a chainlike structure in which the number of the carbon atoms constituting the main chain is from 4 to 20" is from 1 to 10, more preferably from 1 to 5. Preferably, the number of the chainlike structures in which the number of the carbon atoms constituting the main chain is from 4 to 20 is from 1 to 5, more preferably from 1 to 3. Preferably, the chainlike structure in which the number of the carbon atoms constituting the main chain is from 4 to 20 exists at the end of the "group that has both an aromatic ring to form a π-conjugated system with the skeleton to which it bonds, and a chainlike structure in which the number of the carbon atoms constituting the main chain is from 4 to 20". One preferred example is an aromatic group substituted with a group having a chainlike structure in which the number of the carbon atoms constituting the main chain is from 4 to 20, and this may be represented by the following formula (5) or formula (6):

(5)

(6)

In the formula (5), Ar represents an aromatic linking group, including, for example, a phenylene group, a naphthalene group. A preferred example of the group is a p-phenylene group. m indicates an integer of from 4 to 20, and is preferably an integer of from 8 to 20.

In the formula (1), at least one of $R^1$, $R^2$, $R^3$ and $R^4$ represents "a group that has both an aromatic ring to form a π-conjugated system with the skeleton to which it bonds, and a chainlike structure in which the number of the carbon atoms constituting the main chain is from 4 to 20". Preferably, one or two of $R^1$, $R^2$, $R^3$ and $R^4$ each represent "a group that has both an aromatic ring to form a π-conjugated system with the skeleton to which it bonds, and a chainlike structure in which the number of the carbon atoms constituting the main chain is from 4 to 20", and more preferably, two of these each represent "a group that has both an aromatic ring to form a π-conjugated system with the skeleton to which it bonds, and a chainlike structure in which the number of the carbon atoms constituting the main chain is from 4 to 20". In case where two each represent the above, preferably, $R^2$ and $R^4$ each represent "a group that has both an aromatic ring to form a π-conjugated system with the skeleton to which it bonds, and a chainlike structure in which the number of the carbon atoms constituting the main chain is from 4 to 20". In case where two or more of $R^1$, $R^2$, $R^3$ and $R^4$ each represent "a group that has both an aromatic ring to form a π-conjugated system with the skeleton to which it bonds, and a chainlike structure in which the number of the carbon atoms constituting the main chain is from 4 to 20", they may be the same or different. The case where they are the same has the advantage that the compound is easy to produce.

$R^1$, $R^2$, $R^3$ and $R^4$ that are not "a group that has both an aromatic ring to form a π-conjugated system with the skeleton to which it bonds, and a chainlike structure in which the number of the carbon atoms constituting the main chain is from 4 to 20" each independently represent a hydrogen atom or a substituent. In case where two or more of $R^1$, $R^2$, $R^3$ and $R^4$ each are a substituent, they may be the same or different.

The "substituent" in this description may be an electron-donating group or an electron-attracting group. Examples of the electron-donating group include an alkyl group (this may be linear, branched or cyclic, and preferably has from 1 to 20 carbon atoms, more preferably from 1 to 6 carbon atoms; its specific examples include a methyl group, an ethyl group, a propyl group, a pentyl group, a hexyl group, an isopropyl group; and preferred is a methyl group), an alkoxy group (this may be linear, branched or cyclic, and preferably has from 1 to 20 carbon atoms, more preferably from 1 to 6 carbon atoms; and its specific examples include a methoxy group, a hexoxy group), an amino group or a substituted amino group (preferably an amino group substituted with an aromatic group; and its specific examples include a diphenylamino group, an anilino group, a tolylamino group), an aryl group (this may be either monocyclic or condensed cyclic, and may be further substituted with an aryl group; and its specific examples include a phenyl group, a biphenyl group, a terphenyl group), and an electron-donating group containing a heterocyclic structure (preferably an electron-donating group containing a heterocyclic structure that contains a nitrogen atom or a sulfur atom; and its specific examples include a thiophenyl group, a benzothiophenyl group, a julolidyl group, a pyrrolyl group, an indolyl group, a carbazolyl group). Examples of the electron-attracting group include a nitro group, a perfluoroalkyl group (preferably having from 1 to 10 carbon atoms, more preferably from 1 to 6 carbon atoms; and its specific examples include a trifluoromethyl group), a sulfonyl group, an electron-attracting group containing a heterocyclic structure (preferably an electron-attracting group containing a heterocyclic structure that contains a nitrogen atom or a sulfur atom; and its specific examples include an oxadiazolyl group, a benzothiadiazolyl group, a tetrazolyl group, a thiazolyl group, an imidazolyl group, a triazino group), a phosphinoxide structure-containing group, a cyano group, etc. As the substituent, also mentioned is a halogen (concretely, a fluorine atom, a chlorine atom, a bromine atom, an iodine atom).

In the formula (1), $R^1$ and $R^2$ may bond to each other to form a cyclic structure, and $R^3$ and $R^4$ may bond to each other to form a cyclic structure. The cyclic structure includes, for example, a furan ring, a thiophene ring, etc. Preferred is a 5-membered hetero ring that contains an $X^1$ atom.

Taking the matter into consideration that the compound represented by the formula (1) in the invention can be formed into an organic semiconductor layer according to a vapor evaporation method, the molecular weight of the compound is preferably at most 1500, more preferably at most 1200, even more preferably at most 1000. The lower limit of the molecular weight may be, for example, at least 400.

A preferred group of the compounds represented by the formula (1) includes compounds represented by the following formula (2):

(2)

In the formula (2), $X^1$, $X^2$ and $X^3$ each independently represent an oxygen atom, a sulfur atom, a selenium atom or a tellurium atom; $R^1$ and $R^3$ each independently represent a hydrogen atom or a substituent; at least one of $R^{11}$, $R^{12}$, $R^{13}$, $R^{14}$, $R^{15}$, $R^{21}$, $R^{22}$, $R^{23}$, $R^{24}$ and $R^{25}$ represents a group having a chainlike structure in which the number of the carbon atoms constituting the main chain is from 4 to 20, and the remaining ones each independently represent a hydrogen atom or a substituent.

For the description and the preferred range of $X^1$, $X^2$, $X^3$, $R^1$ and $R^3$, referred to is the corresponding description of the formula (1). For the description and the preferred range of the "group having a chainlike structure in which the number of the carbon atoms constituting the main chain is from 4 to 20" and the "substituent" which $R^{11}$, $R^{12}$, $R^{13}$, $R^{14}$, $R^{15}$, $R^{21}$, $R^{22}$, $R^{23}$, $R^{24}$ and $R^{25}$ may have, also referred to is the corresponding description of the formula (1).

In the formula (2), preferably, at least two of $R^{11}$, $R^{12}$, $R^{13}$, $R^{14}$, $R^{15}$, $R^{21}$, $R^{22}$, $R^{23}$, $R^{24}$ and $R^{25}$ each are "a group having a chainlike structure in which the number of the carbon atoms constituting the main chain is from 4 to 20", more preferably from 2 to 6 of these each are "a group having a chainlike structure in which the number of the carbon atoms constituting the main chain is from 4 to 20", even more preferably from 2 to 4 of these each are "a group having a chainlike structure in which the number of the carbon atoms constituting the main chain is from 4 to 20". Also preferably, at least one of $R^{11}$, $R^{12}$, $R^{13}$, $R^{14}$ and $R^{15}$, and at least one of $R^{21}$, $R^{22}$, $R^{23}$, $R^{24}$ and $R^{25}$ each are "a group having a chainlike structure in which the number of the carbon atoms constituting the main chain is from 4 to 20". Above all, preferably, $R^{13}$ and $R^{23}$ each are "a group having a chainlike structure in which the number of the carbon atoms constituting the main chain is from 4 to 20". In case where two or more of the groups each are "a group having a chainlike structure in which the number of the carbon atoms constituting the main chain is from 4 to 20", they may be the same or different. As the "group having a chainlike structure in which the number of the carbon atoms constituting the main chain is from 4 to 20", preferably employed here are those having a structure represented by the above-mentioned formula (5) or formula (6).

Specific examples of the compound represented by the formula (2) are mentioned below. However, the compounds represented by the formula (2) for use in the invention should not be limitatively interpreted by these examples. In the following Tables, S is a sulfur atom, and H is a hydrogen atom.

TABLE 1

| Comp'd No. | $X^1, X^2, X^3$ | $R^1, R^3$ | $R^{11}, R^{15}, R^{21}, R^{25}$ | $R^{12}, R^{14}, R^{22}, R^{24}$ | $R^{13}, R^{23}$ |
|---|---|---|---|---|---|
| 101 | S | H | H | H | n-$C_6H_{13}$— |
| 102 | S | H | H | n-$C_6H_{13}$— | H |
| 103 | S | H | H | $CH_3$ | n-$C_6H_{13}$— |
| 104 | S | H | H | n-$C_6H_{13}$— | $CH_3$ |
| 105 | S | H | H | $CH_3O$— | n-$C_6H_{13}$— |
| 106 | S | H | H | n-$C_6H_{13}$— | $CH_3O$— |
| 107 | S | H | H | n-$C_6H_{13}$— | n-$C_6H_{13}$— |
| 108 | S | H | H | H | n-$C_8H_{17}$— |
| 109 | S | H | H | n-$C_8H_{17}$— | H |
| 110 | S | H | H | $CH_3$ | n-$C_8H_{17}$— |
| 111 | S | H | H | n-$C_8H_{17}$— | $CH_3$ |
| 112 | S | H | H | $CH_3O$— | n-$C_8H_{17}$— |
| 113 | S | H | H | n-$C_8H_{17}$— | $CH_3O$— |
| 114 | S | H | H | n-$C_8H_{17}$— | n-$C_8H_{17}$— |
| 115 | S | H | H | H | n-$C_{10}H_{21}$— |
| 116 | S | H | H | n-$C_{10}H_{21}$— | H |
| 117 | S | H | H | $CH_3$ | n-$C_{10}H_{21}$— |
| 118 | S | H | H | n-$C_{10}H_{21}$— | $CH_3$ |
| 119 | S | H | H | $CH_3O$— | n-$C_{10}H_{21}$— |
| 120 | S | H | H | n-$C_{10}H_{21}$— | $CH_3O$— |
| 121 | S | H | H | n-$C_{10}H_{21}$— | n-$C_{10}H_{21}$— |
| 122 | S | H | H | H | n-$C_{12}H_{25}$— |
| 123 | S | H | H | n-$C_{12}H_{25}$— | H |
| 124 | S | H | H | $CH_3$ | n-$C_{12}H_{25}$— |
| 125 | S | H | H | n-$C_{12}H_{25}$— | $CH_3$ |
| 126 | S | H | H | $CH_3O$— | n-$C_{12}H_{25}$— |
| 127 | S | H | H | n-$C_{12}H_{25}$— | $CH_3O$— |
| 128 | S | H | H | n-$C_{12}H_{25}$— | n-$C_{12}H_{25}$— |
| 129 | S | H | H | H | n-$C_{14}H_{29}$— |
| 130 | S | H | H | n-$C_{14}H_{29}$— | H |
| 131 | S | H | H | $CH_3$ | n-$C_{14}H_{29}$— |
| 132 | S | H | H | n-$C_{14}H_{29}$— | $CH_3$ |
| 133 | S | H | H | $CH_3O$— | n-$C_{14}H_{29}$— |
| 134 | S | H | H | n-$C_{14}H_{29}$— | $CH_3O$— |
| 135 | S | H | H | n-$C_{14}H_{29}$— | n-$C_{14}H_{29}$— |
| 136 | S | H | H | H | n-$C_{20}H_{41}$— |
| 137 | S | H | H | n-$C_{20}H_{41}$— | H |
| 138 | S | H | H | $CH_3$ | n-$C_{20}H_{41}$— |
| 139 | S | H | H | n-$C_{20}H_{41}$— | $CH_3$ |
| 140 | S | H | H | $CH_3O$— | n-$C_{20}H_{41}$— |
| 141 | S | H | H | n-$C_{20}H_{41}$— | $CH_3O$— |
| 142 | S | H | H | n-$C_{20}H_{41}$— | n-$C_{20}H_{41}$— |
| 143 | S | H | $CH_3$ | n-$C_8H_{17}$— | n-$C_8H_{17}$— |
| 144 | S | $CH_3$ | H | n-$C_8H_{17}$— | n-$C_8H_{17}$— |
| 145 | S | H | $CH_3O$ | n-$C_8H_{17}$— | n-$C_8H_{17}$— |
| 146 | S | $CH_3O$ | H | n-$C_8H_{17}$— | n-$C_8H_{17}$— |
| 147 | S | H | $CH_3$ | n-$C_8H_{17}$— | n-$C_8H_{17}$— |
| 148 | S | H | F | n-$C_8H_{17}$— | n-$C_8H_{17}$— |
| 149 | S | F | H | n-$C_8H_{17}$— | n-$C_8H_{17}$— |

TABLE 2

| Comp'd No. | $X^1, X^2, X^3$ | $R^1, R^3$ | $R^{11}, R^{15}, R^{21}, R^{25}$ | $R^{12}, R^{14}, R^{22}, R^{24}$ | $R^{13}, R^{23}$ |
|---|---|---|---|---|---|
| 150 | S | H | H | H | n-$C_6H_{13}O$— |
| 151 | S | H | H | n-$C_6H_{13}O$— | H |
| 152 | S | H | H | $CH_3$ | n-$C_6H_{13}O$— |
| 153 | S | H | H | n-$C_6H_{13}O$— | $CH_3$ |
| 154 | S | H | H | $CH_3O$— | n-$C_6H_{13}O$— |
| 155 | S | H | H | n-$C_6H_{13}O$— | $CH_3O$— |
| 156 | S | H | H | n-$C_6H_{13}O$— | n-$C_6H_{13}O$— |
| 157 | S | H | H | H | n-$C_8H_{17}O$— |
| 158 | S | H | H | n-$C_8H_{17}O$— | H |
| 159 | S | H | H | $CH_3$ | n-$C_8H_{17}O$— |
| 160 | S | H | H | n-$C_8H_{17}O$— | $CH_3$ |
| 161 | S | H | H | $CH_3O$— | n-$C_8H_{17}O$— |
| 162 | S | H | H | n-$C_8H_{17}O$— | $CH_3O$— |
| 163 | S | H | H | n-$C_8H_{17}O$— | n-$C_8H_{17}O$— |
| 164 | S | H | H | H | n-$C_{10}H_{21}O$— |
| 165 | S | H | H | n-$C_{10}H_{21}O$— | H |
| 166 | S | H | H | $CH_3$ | n-$C_{10}H_{21}O$— |
| 167 | S | H | H | n-$C_{10}H_{21}O$— | $CH_3$ |
| 168 | S | H | H | $CH_3O$— | n-$C_{10}H_{21}O$— |
| 169 | S | H | H | n-$C_{10}H_{21}O$— | $CH_3O$— |
| 170 | S | H | H | n-$C_{10}H_{21}O$— | n-$C_{10}H_{21}O$— |
| 171 | S | H | H | H | n-$C_{12}H_{25}O$— |
| 172 | S | H | H | n-$C_{12}H_{25}O$— | H |
| 173 | S | H | H | $CH_3$ | n-$C_{12}H_{25}O$— |
| 174 | S | H | H | n-$C_{12}H_{25}O$— | $CH_3$ |
| 175 | S | H | H | $CH_3O$— | n-$C_{12}H_{25}O$— |
| 176 | S | H | H | n-$C_{12}H_{25}O$— | $CH_3O$— |
| 177 | S | H | H | n-$C_{12}H_{25}O$— | n-$C_{12}H_{25}O$— |
| 178 | S | H | H | H | n-$C_{14}H_{29}O$— |
| 179 | S | H | H | n-$C_{14}H_{29}O$— | H |
| 180 | S | H | H | $CH_3$ | n-$C_{14}H_{29}O$— |
| 181 | S | H | H | n-$C_{14}H_{29}O$— | $CH_3$ |
| 182 | S | H | H | $CH_3O$— | n-$C_{14}H_{29}O$— |
| 183 | S | H | H | n-$C_{14}H_{29}O$— | $CH_3O$— |
| 184 | S | H | H | n-$C_{14}H_{29}O$— | n-$C_{14}H_{29}O$— |
| 185 | S | H | H | H | n-$C_{20}H_{41}O$— |
| 186 | S | H | H | n-$C_{20}H_{41}O$— | H |
| 187 | S | H | H | $CH_3$ | n-$C_{20}H_{41}O$— |
| 188 | S | H | H | n-$C_{20}H_{41}O$— | $CH_3$ |
| 189 | S | H | H | $CH_3O$— | n-$C_{20}H_{41}O$— |
| 190 | S | H | H | n-$C_{20}H_{41}O$— | $CH_3O$— |
| 191 | S | H | H | n-$C_{20}H_{41}O$— | n-$C_{20}H_{41}O$— |
| 192 | S | H | $CH_3$ | n-$C_8H_{17}O$— | n-$C_8H_{17}O$— |
| 193 | S | $CH_3$ | H | n-$C_8H_{17}O$— | n-$C_8H_{17}O$— |
| 194 | S | H | $CH_3O$ | n-$C_8H_{17}O$— | n-$C_8H_{17}O$— |
| 195 | S | $CH_3O$ | H | n-$C_8H_{17}O$— | n-$C_8H_{17}O$— |
| 196 | S | H | $CH_3$ | n-$C_8H_{17}O$— | n-$C_8H_{17}O$— |
| 197 | S | H | F | n-$C_8H_{17}O$— | n-$C_8H_{17}O$— |
| 198 | S | F | H | n-$C_8H_{17}O$— | n-$C_8H_{17}O$— |

TABLE 3

| Comp'd No. | $X^1, X^3$ | $X^2$ | $R^1, R^3$ | $R^{11}, R^{15}, R^{21}, R^{25}$ | $R^{12}, R^{14}, R^{22}, R^{24}$ | $R^{13}, R^{23}$ |
|---|---|---|---|---|---|---|
| 201 | S | Se | H | H | H | n-$C_6H_{13}$— |
| 202 | S | Se | H | H | n-$C_6H_{13}$— | H |
| 203 | S | Se | H | H | $CH_3$ | n-$C_6H_{13}$— |
| 204 | S | Se | H | H | n-$C_6H_{13}$— | $CH_3$ |
| 205 | S | Se | H | H | $CH_3O$— | n-$C_6H_{13}$— |
| 206 | S | Se | H | H | n-$C_6H_{13}$— | $CH_3O$— |
| 207 | S | Se | H | H | n-$C_6H_{13}$— | n-$C_6H_{13}$— |
| 208 | S | Se | H | H | H | n-$C_8H_{17}$— |
| 209 | S | Se | H | H | n-$C_8H_{17}$— | H |
| 210 | S | Se | H | H | $CH_3$ | n-$C_8H_{17}$— |
| 211 | S | Se | H | H | n-$C_8H_{17}$— | $CH_3$ |
| 212 | S | Se | H | H | $CH_3O$— | n-$C_8H_{17}$— |
| 213 | S | Se | H | H | n-$C_8H_{17}$— | $CH_3O$— |
| 214 | S | Se | H | H | n-$C_8H_{17}$— | n-$C_8H_{17}$— |
| 215 | S | Se | H | H | H | n-$C_{10}H_{21}$— |
| 216 | S | Se | H | H | n-$C_{10}H_{21}$— | H |
| 217 | S | Se | H | H | $CH_3$ | n-$C_{10}H_{21}$— |
| 218 | S | Se | H | H | n-$C_{10}H_{21}$— | $CH_3$ |
| 219 | S | Se | H | H | $CH_3O$— | n-$C_{10}H_{21}$— |
| 220 | S | Se | H | H | n-$C_{10}H_{21}$— | $CH_3O$— |
| 221 | S | Se | H | H | n-$C_{10}H_{21}$— | n-$C_{10}H_{21}$— |
| 222 | S | Se | H | H | H | n-$C_{12}H_{25}$— |
| 223 | S | Se | H | H | n-$C_{12}H_{25}$— | H |
| 224 | S | Se | H | H | $CH_3$ | n-$C_{12}H_{25}$— |
| 225 | S | Se | H | H | n-$C_{12}H_{25}$— | $CH_3$ |
| 226 | S | Se | H | H | $CH_3O$— | n-$C_{12}H_{25}$— |
| 227 | S | Se | H | H | n-$C_{12}H_{25}$— | $CH_3O$— |
| 228 | S | Se | H | H | n-$C_{12}H_{25}$— | n-$C_{12}H_{25}$— |
| 229 | S | Se | H | H | H | n-$C_{14}H_{29}$— |
| 230 | S | Se | H | H | n-$C_{14}H_{29}$— | H |

TABLE 3-continued

| Comp'd No. | $X^1, X^3$ | $X^2$ | $R^1, R^3$ | $R^{11}, R^{15}$ $R^{21}, R^{25}$ | $R^{12}, R^{14}$ $R^{22}, R^{24}$ | $R^{13}, R^{23}$ |
|---|---|---|---|---|---|---|
| 231 | S | Se | H | H | $CH_3$ | n-$C_{14}H_{29}$— |
| 232 | S | Se | H | H | n-$C_{14}H_{29}$— | $CH_3$ |
| 233 | S | Se | H | H | $CH_3O$— | n-$C_{14}H_{29}$— |
| 234 | S | Se | H | H | n-$C_{14}H_{29}$— | $CH_3O$— |
| 235 | S | Se | H | H | n-$C_{14}H_{29}$— | n-$C_{14}H_{29}$— |
| 236 | S | Se | H | H | H | n-$C_{20}H_{41}$— |
| 237 | S | Se | H | H | n-$C_{20}H_{41}$— | H |
| 238 | S | Se | H | H | $CH_3$ | n-$C_{20}H_{41}$— |
| 239 | S | Se | H | H | n-$C_{20}H_{41}$— | $CH_3$ |
| 240 | S | Se | H | H | $CH_3O$— | n-$C_{20}H_{41}$— |
| 241 | S | Se | H | H | n-$C_{20}H_{41}$— | $CH_3O$— |
| 242 | S | Se | H | H | n-$C_{20}H_{41}$— | n-$C_{20}H_{41}$— |
| 243 | S | Se | H | $CH_3$ | n-$C_8H_{17}$— | n-$C_8H_{17}$— |
| 244 | S | Se | $CH_3$ | H | n-$C_8H_{17}$— | n-$C_8H_{17}$— |
| 245 | S | Se | H | $CH_3O$ | n-$C_8H_{17}$— | n-$C_8H_{17}$— |
| 246 | S | Se | $CH_3O$ | H | n-$C_8H_{17}$— | n-$C_8H_{17}$— |
| 247 | S | Se | H | $CH_3$ | n-$C_8H_{17}$— | n-$C_8H_{17}$— |
| 248 | S | Se | H | F | n-$C_8H_{17}$— | n-$C_8H_{17}$— |
| 249 | S | Se | F | H | n-$C_8H_{17}$— | n-$C_8H_{17}$— |

TABLE 4

| Comp'd No. | $X^1, X^3$ | $X^2$ | $R^1, R^3$ | $R^{11}, R^{15}$ $R^{21}, R^{25}$ | $R^{12}, R^{14}$ $R^{22}, R^{24}$ | $R^{13}, R^{23}$ |
|---|---|---|---|---|---|---|
| 250 | S | Se | H | H | H | n-$C_6H_{13}O$— |
| 251 | S | Se | H | H | n-$C_6H_{13}O$— | H |
| 252 | S | Se | H | H | $CH_3$ | n-$C_6H_{13}O$— |
| 253 | S | Se | H | H | n-$C_6H_{13}O$— | $CH_3$ |
| 254 | S | Se | H | H | $CH_3O$— | n-$C_6H_{13}O$— |
| 255 | S | Se | H | H | n-$C_6H_{13}O$— | $CH_3O$— |
| 256 | S | Se | H | H | n-$C_6H_{13}O$— | n-$C_6H_{13}O$— |
| 257 | S | Se | H | H | H | n-$C_8H_{17}O$— |
| 258 | S | Se | H | H | n-$C_8H_{17}O$— | H |
| 259 | S | Se | H | H | $CH_3$ | n-$C_8H_{17}O$— |
| 260 | S | Se | H | H | n-$C_8H_{17}O$— | $CH_3$ |
| 261 | S | Se | H | H | $CH_3O$— | n-$C_8H_{17}O$— |
| 262 | S | Se | H | H | n-$C_8H_{17}O$— | $CH_3O$— |
| 263 | S | Se | H | H | n-$C_8H_{17}O$— | n-$C_8H_{17}O$— |
| 264 | S | Se | H | H | H | n-$C_{10}H_{21}O$— |
| 265 | S | Se | H | H | n-$C_{10}H_{21}O$— | H |
| 266 | S | Se | H | H | $CH_3$ | n-$C_{10}H_{21}O$— |
| 267 | S | Se | H | H | n-$C_{10}H_{21}O$— | $CH_3$ |
| 268 | S | Se | H | H | $CH_3O$— | n-$C_{10}H_{21}O$— |
| 269 | S | Se | H | H | n-$C_{10}H_{21}O$— | $CH_3O$— |
| 270 | S | Se | H | H | n-$C_{10}H_{21}O$— | n-$C_{10}H_{21}O$— |
| 271 | S | Se | H | H | H | n-$C_{12}H_{25}O$— |
| 272 | S | Se | H | H | n-$C_{12}H_{25}O$— | H |
| 273 | S | Se | H | H | $CH_3$ | n-$C_{12}H_{25}O$— |
| 274 | S | Se | H | H | n-$C_{12}H_{25}O$— | $CH_3$ |
| 275 | S | Se | H | H | $CH_3O$— | n-$C_{12}H_{25}O$— |
| 276 | S | Se | H | H | n-$C_{12}H_{25}O$— | $CH_3O$— |
| 277 | S | Se | H | H | n-$C_{12}H_{25}O$— | n-$C_{12}H_{25}O$— |
| 278 | S | Se | H | H | H | n-$C_{14}H_{29}O$— |
| 279 | S | Se | H | H | n-$C_{14}H_{29}O$— | H |
| 280 | S | Se | H | H | $CH_3$ | n-$C_{14}H_{29}O$— |
| 281 | S | Se | H | H | n-$C_{14}H_{29}O$— | $CH_3$ |
| 282 | S | Se | H | H | $CH_3O$— | n-$C_{14}H_{29}O$— |
| 283 | S | Se | H | H | n-$C_{14}H_{29}O$— | $CH_3O$— |
| 284 | S | Se | H | H | n-$C_{14}H_{29}O$— | n-$C_{14}H_{29}O$— |
| 285 | S | Se | H | H | H | n-$C_{20}H_{41}O$— |
| 286 | S | Se | H | H | n-$C_{20}H_{41}O$— | H |
| 287 | S | Se | H | H | $CH_3$ | n-$C_{20}H_{41}O$— |
| 288 | S | Se | H | H | n-$C_{20}H_{41}O$— | $CH_3$ |
| 289 | S | Se | H | H | $CH_3O$— | n-$C_{20}H_{41}O$— |
| 290 | S | Se | H | H | n-$C_{20}H_{41}O$— | $CH_3O$— |

TABLE 4-continued

| Comp'd No. | $X^1, X^3$ | $X^2$ | $R^1, R^3$ | $R^{11}, R^{15}$ $R^{21}, R^{25}$ | $R^{12}, R^{14}$ $R^{22}, R^{24}$ | $R^{13}, R^{23}$ |
|---|---|---|---|---|---|---|
| 291 | S | Se | H | H | n-$C_{20}H_{41}O$— | n-$C_{20}H_{41}O$— |
| 292 | S | Se | H | $CH_3$ | n-$C_8H_{17}O$— | n-$C_8H_{17}O$— |
| 293 | S | Se | $CH_3$ | H | n-$C_8H_{17}O$— | n-$C_8H_{17}O$— |
| 294 | S | Se | H | $CH_3O$ | n-$C_8H_{17}O$— | n-$C_8H_{17}O$— |
| 295 | S | Se | $CH_3O$ | H | n-$C_8H_{17}O$— | n-$C_8H_{17}O$— |
| 296 | S | Se | H | $CH_3$ | n-$C_8H_{17}O$— | n-$C_8H_{17}O$— |
| 297 | S | Se | H | F | n-$C_8H_{17}O$— | n-$C_8H_{17}O$— |
| 298 | S | Se | F | H | n-$C_8H_{17}O$— | n-$C_8H_{17}O$— |

TABLE 5

| Comp'd No. | $X^1, X^3$ | $X^2$ | $R^1, R^3$ | $R^{11}, R^{15}$ $R^{21}, R^{25}$ | $R^{12}, R^{14}$ $R^{22}, R^{24}$ | $R^{13}, R^{23}$ |
|---|---|---|---|---|---|---|
| 301 | S | Te | H | H | H | n-$C_6H_{13}$— |
| 302 | S | Te | H | H | n-$C_6H_{13}$— | H |
| 303 | S | Te | H | H | $CH_3$ | n-$C_6H_{13}$— |
| 304 | S | Te | H | H | n-$C_6H_{13}$— | $CH_3$ |
| 305 | S | Te | H | H | $CH_3O$— | n-$C_6H_{13}$— |
| 306 | S | Te | H | H | n-$C_6H_{13}$— | $CH_3O$— |
| 307 | S | Te | H | H | n-$C_6H_{13}$— | n-$C_6H_{13}$— |
| 308 | S | Te | H | H | H | n-$C_8H_{17}$— |
| 309 | S | Te | H | H | n-$C_8H_{17}$— | H |
| 310 | S | Te | H | H | $CH_3$ | n-$C_8H_{17}$— |
| 311 | S | Te | H | H | n-$C_8H_{17}$— | $CH_3$ |
| 312 | S | Te | H | H | $CH_3O$— | n-$C_8H_{17}$— |
| 313 | S | Te | H | H | n-$C_8H_{17}$— | $CH_3O$— |
| 314 | S | Te | H | H | n-$C_8H_{17}$— | n-$C_8H_{17}$— |
| 315 | S | Te | H | H | H | n-$C_{10}H_{21}$— |
| 316 | S | Te | H | H | n-$C_{10}H_{21}$— | H |
| 317 | S | Te | H | H | $CH_3$ | n-$C_{10}H_{21}$— |
| 318 | S | Te | H | H | n-$C_{10}H_{21}$— | $CH_3$ |
| 319 | S | Te | H | H | $CH_3O$— | n-$C_{10}H_{21}$— |
| 320 | S | Te | H | H | n-$C_{10}H_{21}$— | $CH_3O$— |
| 321 | S | Te | H | H | n-$C_{10}H_{21}$— | n-$C_{10}H_{21}$— |
| 322 | S | Te | H | H | H | n-$C_{12}H_{25}$— |
| 323 | S | Te | H | H | n-$C_{12}H_{25}$— | H |
| 324 | S | Te | H | H | $CH_3$ | n-$C_{12}H_{25}$— |
| 325 | S | Te | H | H | n-$C_{12}H_{25}$— | $CH_3$ |
| 326 | S | Te | H | H | $CH_3O$— | n-$C_{12}H_{25}$— |
| 327 | S | Te | H | H | n-$C_{12}H_{25}$— | $CH_3O$— |
| 328 | S | Te | H | H | n-$C_{12}H_{25}$— | n-$C_{12}H_{25}$— |
| 329 | S | Te | H | H | H | n-$C_{14}H_{29}$— |
| 330 | S | Te | H | H | n-$C_{14}H_{29}$— | H |
| 331 | S | Te | H | H | $CH_3$ | n-$C_{14}H_{29}$— |
| 332 | S | Te | H | H | n-$C_{14}H_{29}$— | $CH_3$ |
| 333 | S | Te | H | H | $CH_3O$— | n-$C_{14}H_{29}$— |
| 334 | S | Te | H | H | n-$C_{14}H_{29}$— | $CH_3O$— |
| 335 | S | Te | H | H | n-$C_{14}H_{29}$— | n-$C_{14}H_{29}$— |
| 336 | S | Te | H | H | H | n-$C_{20}H_{41}$— |
| 337 | S | Te | H | H | n-$C_{20}H_{41}$— | H |
| 338 | S | Te | H | H | $CH_3$ | n-$C_{20}H_{41}$— |
| 339 | S | Te | H | H | n-$C_{20}H_{41}$— | $CH_3$ |
| 340 | S | Te | H | H | $CH_3O$— | n-$C_{20}H_{41}$— |
| 341 | S | Te | H | H | n-$C_{20}H_{41}$— | $CH_3O$— |
| 342 | S | Te | H | H | n-$C_{20}H_{41}$— | n-$C_{20}H_{41}$— |
| 343 | S | Te | H | $CH_3$ | n-$C_8H_{17}$— | n-$C_8H_{17}$— |
| 344 | S | Te | $CH_3$ | H | n-$C_8H_{17}$— | n-$C_8H_{17}$— |
| 345 | S | Te | H | $CH_3O$ | n-$C_8H_{17}$— | n-$C_8H_{17}$— |
| 346 | S | Te | $CH_3O$ | H | n-$C_8H_{17}$— | n-$C_8H_{17}$— |
| 347 | S | Te | H | $CH_3$ | n-$C_8H_{17}$— | n-$C_8H_{17}$— |
| 348 | S | Te | H | F | n-$C_8H_{17}$— | n-$C_8H_{17}$— |
| 349 | S | Te | F | H | n-$C_8H_{17}$— | n-$C_8H_{17}$— |

TABLE 6

| | | | | Formula (2) | | |
|---|---|---|---|---|---|---|
| Comp'd No. | $X^1$, $X^3$ | $X^2$ | $R^1$, $R^3$ | $R^{11}$, $R^{15}$ $R^{21}$, $R^{25}$ | $R^{12}$, $R^{14}$ $R^{22}$, $R^{24}$ | $R^{13}$, $R^{23}$ |
| 350 | S | Te | H | H | H | n-$C_6H_{13}$O— |
| 351 | S | Te | H | H | n-$C_6H_{13}$O— | H |
| 352 | S | Te | H | H | $CH_3$ | n-$C_6H_{13}$O— |
| 353 | S | Te | H | H | n-$C_6H_{13}$O— | $CH_3$ |
| 354 | S | Te | H | H | $CH_3$O— | n-$C_6H_{13}$O— |
| 355 | S | Te | H | H | n-$C_6H_{13}$O— | $CH_3$O— |
| 356 | S | Te | H | H | n-$C_6H_{13}$O— | n-$C_6H_{13}$O— |
| 357 | S | Te | H | H | H | n-$C_8H_{17}$O— |
| 358 | S | Te | H | H | n-$C_8H_{17}$O— | H |
| 359 | S | Te | H | H | $CH_3$ | n-$C_8H_{17}$O— |
| 360 | S | Te | H | H | n-$C_8H_{17}$O— | $CH_3$ |
| 361 | S | Te | H | H | $CH_3$O— | n-$C_8H_{17}$O— |
| 362 | S | Te | H | H | n-$C_8H_{17}$O— | $CH_3$O— |
| 363 | S | Te | H | H | n-$C_8H_{17}$O— | n-$C_8H_{17}$O— |
| 364 | S | Te | H | H | H | n-$C_{10}H_{21}$O— |
| 365 | S | Te | H | H | n-$C_{10}H_{21}$O— | H |
| 366 | S | Te | H | H | $CH_3$ | n-$C_{10}H_{21}$O— |
| 367 | S | Te | H | H | n-$C_{10}H_{21}$O— | $CH_3$ |
| 368 | S | Te | H | H | $CH_3$O— | n-$C_{10}H_{21}$O— |
| 369 | S | Te | H | H | n-$C_{10}H_{21}$O— | $CH_3$O— |
| 370 | S | Te | H | H | n-$C_{10}H_{21}$O— | n-$C_{10}H_{21}$O— |
| 371 | S | Te | H | H | H | n-$C_{12}H_{25}$O— |
| 372 | S | Te | H | H | n-$C_{12}H_{25}$O— | H |
| 373 | S | Te | H | H | $CH_3$ | n-$C_{12}H_{25}$O— |
| 374 | S | Te | H | H | n-$C_{12}H_{25}$O— | $CH_3$ |
| 375 | S | Te | H | H | $CH_3$O— | n-$C_{12}H_{25}$O— |
| 376 | S | Te | H | H | n-$C_{12}H_{25}$O— | $CH_3$O— |
| 377 | S | Te | H | H | n-$C_{12}H_{25}$O— | n-$C_{12}H_{25}$O— |
| 378 | S | Te | H | H | H | n-$C_{14}H_{29}$O— |
| 379 | S | Te | H | H | n-$C_{14}H_{29}$O— | H |
| 380 | S | Te | H | H | $CH_3$ | n-$C_{14}H_{29}$O— |
| 381 | S | Te | H | H | n-$C_{14}H_{29}$O— | $CH_3$ |
| 382 | S | Te | H | H | $CH_3$O— | n-$C_{14}H_{29}$O— |
| 383 | S | Te | H | H | n-$C_{14}H_{29}$O— | $CH_3$O— |
| 384 | S | Te | H | H | n-$C_{14}H_{29}$O— | n-$C_{14}H_{29}$O— |
| 385 | S | Te | H | H | H | n-$C_{20}H_{41}$O— |
| 386 | S | Te | H | H | n-$C_{20}H_{41}$O— | H |
| 387 | S | Te | H | H | $CH_3$ | n-$C_{20}H_{41}$O— |
| 388 | S | Te | H | H | n-$C_{20}H_{41}$O— | $CH_3$ |
| 389 | S | Te | H | H | $CH_3$O— | n-$C_{20}H_{41}$O— |
| 390 | S | Te | H | H | n-$C_{20}H_{41}$O— | $CH_3$O— |
| 391 | S | Te | H | H | n-$C_{20}H_{41}$O— | n-$C_{20}H_{41}$O— |
| 392 | S | Te | H | $CH_3$ | n-$C_8H_{17}$O— | n-$C_8H_{17}$O— |
| 393 | S | Te | $CH_3$ | H | n-$C_8H_{17}$O— | n-$C_8H_{17}$O— |
| 394 | S | Te | H | $CH_3$O | n-$C_8H_{17}$O— | n-$C_8H_{17}$O— |
| 395 | S | Te | $CH_3$O | H | n-$C_8H_{17}$O— | n-$C_8H_{17}$O— |
| 396 | S | Te | H | $CH_3$ | n-$C_8H_{17}$O— | n-$C_8H_{17}$O— |
| 397 | S | Te | H | F | n-$C_8H_{17}$O— | n-$C_8H_{17}$O— |
| 398 | S | Te | F | H | n-$C_8H_{17}$O— | n-$C_8H_{17}$O— |

[Method for Producing Compounds Represented by Formula (2)]

The novel compounds represented by the formula (2) can be produced by suitably combining known production methods as necessary. For example, a compound represented by the following formula (7) is reacted with n-butyllithium, and then reacted with 2-isopropoxy-4,4,5,5-tetramethyl-1,3,2-dioxabororane, and the resulting compound is further reacted with a compound represented by the following formula (9) to give the intended compound. According to the production method, there can be produced a compound of the formula (2) in which $R^{11}$ and $R^{21}$ are the same, $R^{12}$ and $R^{22}$ are the same, $R^{13}$ and $R^{23}$ are the same, $R^{14}$ and $R^{24}$ are the same, and $R^{15}$ and $R^{25}$ are the same. In this, when a compound of the formula (9) where $X^1$ and $X^3$ are the same is used, a symmetric compound of the formula (2) can be produced. On the other hand, when a mixture of a compound of the formula (7) and a compound of the following formula (8) has a different structure from the former is used in place of using the compound of the formula (7) alone, then an asymmetric compound of the formula (2) can be produced.

Regarding the specific production method and the specific production condition for the compounds of the formula (2), referred to are the description of Production Examples given below. The production method and the production condition can be suitably changed or optimized within a range self-known to those skilled in the art. In addition, the compounds of the formula (2) can also be produced with reference to publications that disclose production methods for compounds having similar structures. For example, the compounds can be produced by applying thereto the production methods described in paragraph [0027] of JP-A-2006-89413 and in the Production Examples in JP-A 2006-89413.

The produced compounds of the formula (2) can be purified according to known purification methods of chromatography, recrystallization, etc.

(7)

(8)

(9)

The definitions of $R^1$, $R^3$, $R^{11}$, $R^{12}$, $R^{13}$, $R^{14}$, $R^{15}$, $R^{21}$, $R^{22}$, $R^{23}$, $R^{24}$, $R^{25}$, $X^1$, $X^2$ and $X^3$ in the formulae (7) to (9) are the same as the definitions in the formula (1) and the formula (2).

[Organic Semiconductor Device]

The organic semiconductor device of the invention is characterized by having an organic semiconductor layer that contains a compound represented by the formula (1). One preferred embodiment of the organic semiconductor device is a field-effect transistor. A typical field-effect transistor comprises a gate electrode provided on a substrate, a gate insulation layer provided on the gate electrode, an organic semiconductor layer provided so as to be spaced from the gate electrode by the gate insulation layer, and a source electrode and a drain electrode provided so as to be adjacent to the organic semiconductor layer. These members are described below.

(1) Gate Electrode

Not specifically defined, the constitutive material for the gate electrode may be any electroconductive material, for which any known material is suitably selected in any desired manner. Examples of the material of the gate electrode include metals such as platinum, gold, aluminium, chromium, nickel, copper, titanium, magnesium, calcium, barium, sodium, etc.; electroconductive metal oxides such as $InO_2$, $SnO_2$, ITO, etc.; doped electroconductive polymers such as camphorsulfonic acid-doped polyaniline, paratoluenesulfonic acid-doped polyethylene dioxythiophene, etc.; electroconductive composite materials prepared by dispersing carbon black, graphite powder, metal fine particles or the like in a binder, etc. One alone or two or more of these materials may be used here either singly or as combined in any desired ratio.

The gate electrode may be formed, for example, according to a vacuum evaporation method, a sputtering method, a coating method, a printing method, a sol-gel method, etc. The patterning method for the gate electrode includes, for example, a photolithographic method that comprises a combination of photoresist patterning and etching with an etching liquid or reactive plasma; a printing method of inkjet printing, screen printing, offset printing, relief printing, etc.; a soft lithographic method such as a micro-contact printing method, etc.; and a method comprising a combination of those methods. Direct patterning is also employable here, which comprises irradiation with energy rays such as laser, electron beams or the like for material removal or for varying the electroconductivity of the irradiated material.

Not specifically defined, the thickness of the gate electrode may be generally at least 0.01 µm, but is preferably at least 0.02 µm, and may be generally at most 2 µm, but is preferably at most 1 µm.

(2) Gate Insulation Layer

The gate insulation layer is a layer having the function of securing the overlapping region between the gate electrode, and the source electrode and the drain electrode, as well as the channel region on the gate electrode, as an electric insulation region. "Electric insulation" as referred to herein means that the electroconductivity is at most $10^{-9}$ S/cm.

Not specifically defined, the material of the gate insulation layer may be any material having insulation performance. For example, there are mentioned polymers such as polymethyl (meth)acrylate, polystyrene, polyvinylphenol, polyimide, polycarbonate, polyester, polyvinyl alcohol, polyvinyl acetate, polyurethane, polysulfone, polyimide resin, polyamide resin, epoxy resin, phenolic resin, etc., and copolymers prepared by combining them; oxides such as silicon dioxide, aluminium oxide, titanium oxide, etc.; ferroelectric oxides such as $SrTiO_3$, $BaTiO_3$, etc.; other dielectrics such as nitrides, e.g., silicon nitride, and sulfides, fluorides, etc.; polymers in which particles of such dielectric material are dispersed, etc. One alone or two or more different types of these materials may be used here either singly or as combined in any desired ratio.

The gate insulation layer has some influence on the leak current to the gate electrode and on the low gate voltage driving capability of the field-effect transistor, and therefore, the electroconductivity thereof at room temperature is preferably at most $10^{-9}$ S/cm, more preferably at most $10^{-14}$ S/cm. Also preferably, the specific permittivity of the gate insulation layer is, in general, at least 2.0, more preferably at least 2.5.

The gate insulation layer may be formed through solution treatment according to a known method of spin coating, solution casting, stamp printing, screen printing, jet printing or the like followed by drying to form an uncrosslinked polymer layer, and thereafter through UV irradiation at a dose of at least 10 mJ/cm$^2$ or through heat treatment to form a crosslinked structure in the layer, thereby giving a crosslinked polymer layer. For example, during crosslinking treatment through UV irradiation, a photomask or the like may be used for patterning, and the uncrosslinked polymer part not irradiated with UV ray can be readily removed with an organic solvent or the like. The patterning treatment facilitates construction of a via-hole structure in the driving circuit in a display device.

The thickness of the gate insulation layer may be generally at least 0.01 µm but is preferably at least 0.1 µm, more preferably at least 0.2 µm, and may be generally at most 4 µm, preferably at most 2 µm, more preferably at most 1 µm.

(3) Organic Semiconductor Layer

The organic semiconductor layer can be formed according to a method of crystallizing a compound of the above-mentioned formula (1) from a solution of the compound (recrystallization method). The solvent to be used in this is an organic solvent capable of dissolving the compound of the formula (1). For example, preferred are halogen solvents having a halogen atom, and aromatic solvents having an aromatic ring. Concretely, there are mentioned halogenobenzenes such as dichlorobenzene, etc. The compound of the formula (1) may be dissolved in the solvent at room temperature of optionally with heating to give a solution thereof. The solution may be applied onto a substrate according to a method suitably selected from ordinary methods generally employed in the art. The substrate as referred to herein is a concept that broadly includes materials before formation of the organic semiconductor layer thereon, naturally including those where some other layer has been formed on a support. For example, for forming the organic semiconductor layer on the substrate, employable here are coating methods of casting, spin coating, dip coating, blade coating, wire bar coating, spray coating or the like; printing methods of inkjet printing, screen printing, offset printing, relief printing or the like; soft lithographic methods such as a micro-contact printing method or the like; and other methods comprising a combination of those methods. Subsequently, the compound is crystallized out from the coating solution, and then, if desired, heated optionally under reduced pressure to remove the solvent. The organic semiconductor layer thus formed according to the recrystallization method where the intended compound is crystallized out from the solution thereof can have a noticeably higher carrier mobility than that of the organic semiconductor layer formed according to a vacuum evaporation method, and can therefore have a large on/off ratio.

The organic semiconductor layer can also be formed by the use of the novel compound of the above-mentioned formula (2) according to any desired method. In case where the compound of the formula (2) is used, the organic semiconductor layer may be formed according to the recrystallization method of crystallizing the compound from a solution thereof as in the above, or may be formed according to any other method such as a vacuum process or the like. For the vacuum process, for example, a vacuum evaporation method is employable where the organic semiconductor material is put in a crucible or a metal boat and heated therein in vacuum so as to be deposited on the substrate or the like. In this case, the vacuum degree may be at most $1\times10^{-3}$ Torr, but preferably at most $1\times10^{-5}$ Torr. Since the substrate temperature has some influence on the properties of the transistor to be produced, it is desirable that the optimum substrate temperature is selected. In general, the substrate temperature preferably falls within a range of from 0° C. to 200° C. The evaporation rate is generally at least 0.01 angstrom/sec, but preferably at least 0.1 angstrom/sec, and is generally at most 100 angstrom/sec, preferably at most 10 angstrom/sec. As the method of evaporating the material, herein employable is heating as well as a sputtering method where accelerated ions of argon or the like are made to collide against the material. The organic semiconductor layer formed by the use of the compound of the formula (2) has a relatively higher carrier mobility than that of the organic semiconductor layer formed by the use of any other similar compound according to the same method, and therefore tends to have a large on/off ratio.

Regarding the thickness of the organic semiconductor layer, when the layer is too thin, then the part thereof through which current can run would be limited and the characteristics of the layer would be insufficient; however, when too thick, the material necessary for layer formation would increase and the layer formation time would be long thereby causing production cost increase, and in addition, an off-current may readily run through the layer so that the layer could not realize a large on/off ratio. Accordingly, the preferred thickness of the organic semiconductor layer is generally at least 5 nm, more preferably at least 10 nm, even more preferably at least 30 nm, and is generally at most 10 more preferably at most 1 µm, even more preferably at most 500 nm.

(4) Source Electrode and Drain Electrode

Not specifically defined, the constituent material of the source electrode and the drain electrode may be any electroconductive material like that of the gate electrode, for which any known material can be selected and used in any desired manner. Examples of the material of the source electrode and the drain electrode include metals such as platinum, gold, aluminiuM, chromium, nickel, copper, titanium, magnesium, calcium, barium, sodium, etc.; electroconductive metal oxides such as $InO_2$, $SnO_2$, ITO, etc.; doped electroconductive polymers such as camphorsulfonic acid-doped polyaniline, paratoluenesulfonic acid-doped polyethylene dioxythiophene, etc.; electroconductive composite materials prepared by dispersing carbon black, graphite powder, metal fine particles or the like in a binder, etc. One alone or two or more of these materials may be used here either singly or as combined in any desired ratio.

Like the gate electrode, the source electrode and the drain electrode may be formed, for example, according to a vacuum evaporation method, a sputtering method, a coating method, a printing method, a sol-gel method, etc. The patterning method for the electrode includes, for example, a photolithographic method that comprises a combination of photoresist patterning and etching with an etching liquid or reactive plasma; a printing method of inkjet printing, screen printing, offset printing, relief printing, etc.; a soft lithographic method such as a micro-contact printing method, etc.; and a method comprising a combination of those methods. Direct patterning is also employable here, which comprises irradiation with energy rays such as laser, electron beams or the like for material removal or for varying the electroconductivity of the irradiated material.

Not specifically defined, the thickness of the source electrode and the drain electrode may be generally at least 0.01 µm, but is preferably at least 0.02 µm, and may be generally at most 2 µm, but is preferably at most 1 µm.

(5) Channel

In the organic field-effect transistor, the current running through the channel part sandwiched between the source electrode and the drain electrode is controlled by the gate electrode for switching or amplification. When the length of the channel part (gap distance between the source electrode and the drain electrode) is narrower, in general, the characteristics of the transistor could be better; but when the length is too narrow, then the off current may increase or the on/off ratio may reduce, or that is, there may occur a so-called short channel effect. On the other hand, when the width of the channel (width between the source electrode and the drain electrode) is large, then it is advantageous in that a large current could run therethrough; but when too large, the area of the device may increase and it is disadvantageous in point of the device integration. When the source electrode and the drain electrode are so planned as to have a comb-shaped structure, then a long channel length could be realized.

Accordingly, the channel length may be generally at least 100 nm, preferably at least 500 nm, more preferably at least 1 µm, and may be generally at most 1 mm, preferably at most 100 µm, more preferably at most 50 µm. The channel width may be generally at least 500 nm, preferably at least 5 µm, more preferably at least 10 µm, and may be generally at most 20 mm, preferably at most 5 mm, more preferably at most 1 mm.

The structure and the constituent material for the field-effect transistor of the invention are not limited to those described above, and any other known structure and material than the above can be suitably selected for use herein. In addition, any change and modification self-obvious to those skilled in the art can be made herein.

The field-effect transistor of the invention has a higher carrier mobility and has a larger on/off ratio, as compared with other field-effect transistors similar to the invention. The carrier mobility of the field-effect transistor of the invention is, for example, more than 0.2 $cm^2/Vs$, and may often reach more than 10 $cm^2/Vs$, or even more than 25 $cm^2/Vs$. The on/off ratio of the field-effect transistor of the invention is, for example, more than $1\times10^6$, and may often reach $5.0\times10^7$ or more.

EXAMPLES

The characteristics of the invention are described more concretely with reference to Synthesis Examples, Examples and Comparative Examples given below. In the following Synthesis Examples and Examples, the materials used, the details of the treatment and the treatment process may be suitably modified or changed not overstepping the spirit and the scope of the invention. Accordingly, the invention should not be limitatively interpreted by the Examples mentioned below.

Synthesis Example 1

Synthesis of DTT-8

DTT-8

Synthesis of Compound 2

N-bromosuccinimide (5.87 g, 33 mmol) was gradually added to a solution of the compound 1 (by Aldrich, 2.94 g, 15 mmol) in dewatered DMF (60 mL) at 0° C. The mixture was heated up to room temperature, stirred overnight, and then poured into water, and the formed precipitate was taken out. This was washed with methanol and recrystallized in chloroform/methanol to give an off-white crystal of the compound 2 (yield: 5.14 g, 97%).

$^1$H NMR (500 MHz, CDCl$_3$): δ 7.28 (s, 2H).

Synthesis of Compound 4

A hexane solution of n-butyllithium (1.65 M, 40 mL, 66 mmol) was dropwise added to a dewatered THF (400 mL) solution of the compound 3 (by Wako Pure Chemicals, 16.2 g, 60 mmol) at −78° C., and the mixture was reacted for 1 hour. Next, 2-isopropoxy-4,4,5,5-tetramethyl-1,3,2-dioxabororane (16.8 g, 90 mmol) was added thereto and stirred overnight at room temperature, and then poured into water and extracted with hexane. The organic phase was washed with water, dried with anhydrous sodium sulfate, and then the solvent was evaporated away. The residue was purified through silica gel chromatography (eluent: hexane/ethyl acetate=10/1 (v/v)) and then dried in vacuum to give a colorless oil of the compound 4 (yield: 17.5 g, 92%).

Synthesis of DTT-8

Pd(PPh$_3$)$_4$ (0.92 g, 0.8 mmol) and aqueous solution of K$_2$CO$_3$ (2.0 M, 30 mL) were added to a dewatered THF (60 mL) solution of the compound 2 (2.83 g, 8.0 mmol) and the compound 4 (5.57 g, 17.6 mmol). The mixture was vigorously stirred at 60° C. for 24 hours, then cooled to room temperature, poured into water and extracted with chloroform. The organic phase was washed with water, dried with anhydrous sodium sulfate, then the solvent was evaporated away, and the residue was purified through silica gel chromatography (eluent: chloroform), then recrystallized in chloroform/acetone and dried in vacuum to give a yellow crystal of DTT-8 (yield: 4.08 g, 89%). The obtained crystal was purified through sublimation and then used in the next synthesis.

$^1$H NMR (500 MHz, CDCl$_3$): δ 7.55 (d, J=8.0 Hz, 4H), 7.46 (s, 2H), 7.22 (d, J=8.0 Hz, 4H), 2.63 (t, J=7.6 Hz, 4H), 1.70-1.60 (m, 4H), 1.40-1.20 (m, 20H), 0.89 (t, J=6.5 Hz, 6H).

Anal. calcd (%) for C$_{36}$H$_{44}$S$_3$: C, 75.47, H, 7.74, S 16.79. found: C, 75.42, H, 7.69, S 16.89.

Synthesis Example 2

Synthesis of TT-8

TT-8

Synthesis of TT-8

Pd(PPh$_3$)$_4$ (0.34 g, 0.3 mmol) and aqueous solution of K$_2$CO$_3$ (2.0 M, 20 mL) were added to a dry THF (40 mL) solution of the compound 5 (by Aldrich, 0.89 g, 3.0 mmol) and the compound 4 (1.99 g, 6.3 mmol). The mixture was vigorously stirred at 60° C. for 36 hours, then cooled to room temperature, poured into water and extracted with chloroform. The organic phase was washed with water, dried with anhydrous sodium sulfate, then the solvent was evaporated away, and the residue was purified through silica gel chromatography (eluent: chloroform), then recrystallized in chloroform/methanol and dried in vacuum to give a pale yellow solid of TT-8 (yield: 1.03 g, 66%).

$^1$H NMR (500 MHz, CDCl$_3$): δ 7.54 (d, J=7.8 Hz, 4H), 7.42 (s, 2H), 7.21 (d, J=7.8 Hz, 4H), 2.62 (t, J=7.6 Hz, 4H), 1.64-1.54 (m, 4H), 1.32-1.25 (m, 20H), 0.88 (t, J=6.5 Hz, 6H).

Anal. calcd (%) for C$_{34}$H$_{44}$S$_2$: C, 79.01, H, 8.58, S 12.41. found: C, 79.08, H, 8.57, S 12.35.

Synthesis Example 3

Synthesis of DTTe-8

DTTe-8

Synthesis of DTTe-8

The compound 6 (0.35 g, 0.5 mmol) was dissolved in dewatered THF (20 mL), cooled to −78° C., then n-butyllithium/hexane (1.62 M, 0.7 mL, 1.1 mmol) was dropwise added thereto and stirred at −78° C. for 1 hour. Next, tellurium (0.08 g, 0.65 mmol) was added thereto and stirred overnight at room temperature. The reaction solution was poured into pure water, extracted with chloroform, dried with anhydrous sodium sulfate, and the solution was filtered and then the solvent was evaporated away with an evaporator. The obtained crude product was purified through column chromatography (developing solvent: hexane/chloroform=8/1), and then recrystallized in chloroform/methanol to give a pale yellow solid of DTTe-8 (yield: 0.02 g, 6%).

$^1$H NMR (500 MHz, CDCl$_3$): δ 7.55 (d, J=8.0 Hz, 4H), 7.50 (s, 2H), 7.22 (d, J=8.0 Hz, 4H), 2.63 (t, J=7.8 Hz, 4H), 1.67-1.60 (m, 4H), 1.35-1.25 (m, 20H), 0.88 (t, J=7.0 Hz, 6H). MS (MALDI): m/z 670.2 [M]$^+$; calcd 670.19.

Example 1

Production of Field-Effect Transistor Using DTT-8

An n$^{++}$-Si substrate with a 300-nm thermal oxidation film (SiO$_2$:C$_i$=1.15×10$^{-8}$ F/cm$^2$) was used as an insulation film and a gate electrode. The substrate size was 15 mm×15 mm square. The substrate was immersed in hydrogen peroxide/sulfuric acid=¼ (v/v) put in a laboratory dish, and heated at 100° C. for 30 minutes to remove the contaminant from the substrate surface. Subsequently, this was washed with a large quantity of ion-exchanged water. Next, the substrate was ultrasonically washed with acetone and then 2-propanol for 5 minutes each, and finally washed with boiling propanol for 10 minutes. Subsequently, for removing organic matters from the surface thereof, the substrate was washed with UV/O$_3$ for 15 minutes.

Aldrich's product, polymethylmethacrylate (PMMA) having a degree of polymerization Mw=79,000 was used here. The solvent for the PMMA solution was toluene, and the concentration thereof was 10 mg/ml. The pulling-up rate was 1 mm/sec. After the immersion, the substrate was heated in a glove box at 80° C. for 8 hours to thereby remove the solvent. DTT-8 synthesized in Synthesis Example 1 was dissolved in 1,2-dichlorobenzene to have a controlled concentration of 0.5% by weight, and then drop-cast in the glove box to grow a single crystal in 68 nm in the glove box.

The substrate was transferred from the glove box to a metal chamber, depressurized to 10$^{-4}$ Pa, and Au was deposited thereon in a mode of vacuum evaporation via a metal mask (about 0.1 nm/sec, 500 nm). Accordingly, there was produced a field-effect transistor with a DTT-8 layer formed thereon according to a recrystallization method.

Figure 1:
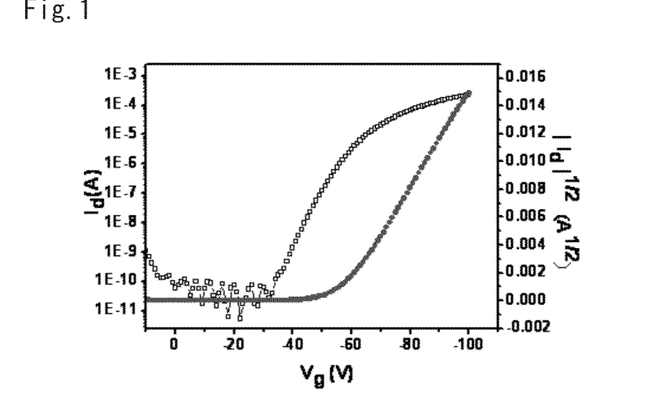
FIG. 1 is a graph showing the $I_d$-$V_g$ characteristic of the field-effect transistor of Example 1.
Figure 2:
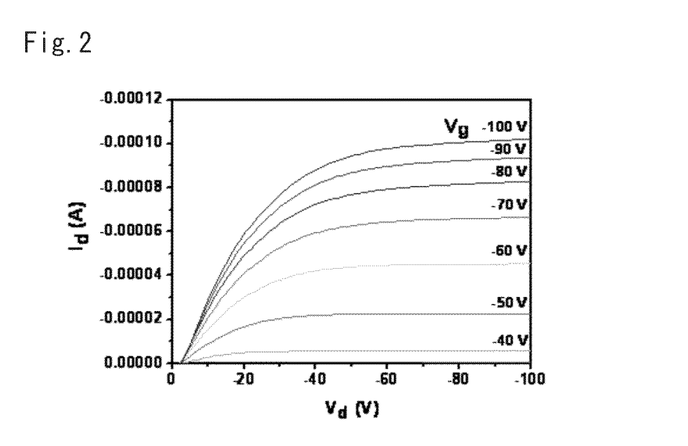
FIG. 2 is a graph showing the $I_d$-$V_d$ characteristic of the field-effect transistor of Example 1.

The channel length and the channel width of the single crystal were measured with an optical microscope. The device was analyzed with an analyzer (Agilent's Semiconductor Device Analyzer B1500) in an air atmosphere. In a state where a fixed voltage of −100 V was kept applied to the drain electrode, the gate voltage was swept from +5 V to −100 V and the I$_d$-V$_g$ characteristic data of the device were measured. The results are shown in FIG. 1. On the other hand, V$_d$ was scanned while V$_g$ was stepwise controlled from −40 V to −100 V at intervals of 10 V, and the I$_d$-V$_d$ characteristic data of the device were measured. The results are shown in FIG. 2. The carrier mobility was 27.0 cm$^2$/Vs, the on/off ratio was 5×10$^7$, and the threshold voltage was −50.1 V.

Using a toluene solution of PMMA, an insulation film was formed on a substrate of Si with an SiO$_2$ film formed thereon; and on this, a 50-nm thick DTT-8 was formed through vacuum evaporation, and Au was further thereon also through vacuum evaporation. Accordingly, there was produced a field-effect transistor having a DTT-8 film formed thereon according to a vacuum evaporation method. In the same manner as above, the I$_d$-V$_g$ characteristic data and the I$_d$-V$_d$ characteristic data of the device were measured. The carrier mobility was 0.26 cm$^2$/Vs, the on/off ratio was 4×10$^6$, and the threshold voltage was −21.2 V.

The above confirm that the field-effect transistor using the compound of the invention shows a high mobility even when the semiconductor layer was formed therein according to a vacuum evaporation method, but when the semiconductor layer was formed according to a recrystallization method, the carrier mobility can be more remarkably increased. It has also been confirmed that, when the vacuum evaporation method is changed to the recrystallization method, the on/off ratio is also increased.

Comparative Example 1

Production of Field-Effect Transistor Using TT-8

Field-effect transistors were produced and evaluated according to the vacuum evaporation method and the recrystallization method but using TT-8 synthesized in Synthesis Example 2 in place of DTT-8. As a result, the data shown in Table 7 below were found.

Comparative Example 2

Production of Field-Effect Transistor Using BT-8

Field-effect transistors were produced and evaluated according to the vacuum evaporation method and the recrystallization method but using a known compound BT-8 in place of DTT-8. As a result, the data shown in Table 7 below were found.

BT-8

In Example 1, the carrier mobility and the on/off ratio of the device produced according to the recrystallization method were both remarkably higher than those of the device produced according to the vacuum evaporation method; but in Comparative Examples 1 and 2, the carrier mobility and the on/off ratio of the devices produced according to the recrystallization method were lower than those of the devices produced according to the vacuum evaporation method.

The organic semiconductor device of the invention has a high carrier mobility and has a large on/off ratio. Another advantage of the invention is that the device can be produced inexpensively and in a simplified manner. Accordingly, the industrial applicability of the invention is great.

While the present invention has been described in detail and with reference to specific embodiments thereof, it will be apparent to one skilled in the art that various changes and modifications can be made therein without departing from the spirit and scope thereof.

The present disclosure relates to the subject matter contained in Japanese Patent Application No. 049633/2002 filed on Feb. 26, 2002 and Japanese Patent Application No. 2012-30705, filed on Feb. 15, 2012, the contents of which are expressly incorporated herein by reference in their entirety.

All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. An organic semiconductor device which has an organic semiconductor layer formed by crystallizing a compound represented by the following formula (1) from a solution of the compound:

(1)

wherein $X^1$, $X^2$ and $X^3$ each independently represent an oxygen atom, a sulfur atom, a selenium atom or a tellurium atom; at least one of $R^1$, $R^2$, $R^3$ and $R^4$ represents a group that has both an aromatic ring to form a π-conjugated system with the skeleton to which it bonds, and a chainlike structure in which the number of the carbon atoms constituting the main chain is from 4 to 20, and the remaining ones each independently represent a hydrogen atom or a substituent; $R^1$ and $R^2$ may bond to each other to form a cyclic structure, and $R^3$ and $R^4$ may bond to each other to form a cyclic structure.

2. The organic semiconductor device according to claim 1, wherein the organic semiconductor layer is formed by crystallizing a compound represented by the following formula (2) from a solution of the compound:

(2)

wherein $X^1$, $X^2$ and $X^3$ each independently represent an oxygen atom, a sulfur atom, a selenium atom or a tellurium atom; $R^1$ and $R^3$ each independently represent a hydrogen atom or a substituent; at least one of $R^{11}$, $R^{12}$, $R^{13}$, $R^{14}$, $R^{15}$, $R^{21}$, $R^{22}$, $R^{23}$, $R^{21}$ and $R^{25}$ represents a group having a chainlike structure of which the number of the atoms of the main chain is from 4 to 20, and the remaining ones each independently represent a hydrogen atom or a substituent.

3. The organic semiconductor device according to claim 2, wherein the group having a chainlike structure in which the number of the carbon atoms constituting the main chain is from 4 to 20 has a structure represented by the following formula (5):

H—(CH$_2$)$_m$—Ar— (5)

wherein Ar represents an aromatic linking group; and m indicates an integer of from 4 to 20.

4. The organic semiconductor device according to claim 2, wherein the group having a chainlike structure in which the number of the carbon atoms constituting the main chain is from 4 to 20 has a structure represented by the following formula (6):

H—(CH$_2$)$_m$O—Ar— (6)

wherein Ar represents an aromatic linking group; and m indicates an integer of from 4 to 20.

5. The organic semiconductor device according to claim 2, wherein at least one of $R^{13}$ and $R^{23}$ is a group having a chainlike structure in which the number of the carbon atoms constituting the main chain is from 4 to 20.

6. The organic semiconductor device according to claim 2, wherein at least one of $R^{13}$ and $R^{23}$ is a group having a chainlike structure in which the number of the carbon atoms constituting the main chain is from 8 to 20.

7. The organic semiconductor device according to claim 1, wherein $X^1$, $X^2$ and $X^3$ are the same atoms.

8. The organic semiconductor device according to claim 7, wherein $X^1$, $X^2$ and $X^3$ are sulfur atoms.

9. The organic semiconductor device according to claim 1, wherein $X^1$ and $X^3$ are sulfur atoms and $X^2$ is a selenium atom or a tellurium atom.

10. The organic semiconductor device according to claim 1, which is a field-effect transistor.

11. A method for producing an organic semiconductor device, which comprises forming an organic semiconductor layer by crystallizing a compound represented by the following formula (1) from a solution of the compound:

(1)

wherein $X^1$, $X^2$ and $X^3$ each independently represent an oxygen atom, a sulfur atom, a selenium atom or a tellurium atom; at least one of $R^1$, $R^2$, $R^3$ and $R^4$ represents a group that has both an aromatic ring to form a π-conjugated system with the skeleton to which it bonds, and a chainlike structure in which the number of the carbon atoms constituting the main chain is from 4 to 20, and the remaining ones each independently represent a hydrogen atom or a substituent; $R^1$ and $R^2$ may bond to each other to form a cyclic structure, and $R^3$ and $R^4$ may bond to each other to form a cyclic structure.

12. The method for producing an organic semiconductor device according to claim 11, wherein the organic semiconductor layer is formed by crystallizing a compound represented by the following formula (2) from a solution of the compound:

(2)

wherein $X^1$, $X^2$ and $X^3$ each independently represent an oxygen atom, a sulfur atom, a selenium atom or a tellurium atom; $R^1$ and $R^3$ each independently represent a hydrogen atom or a substituent; at least one of $R^{11}$, $R^{12}$, $R^{13}$, $R^{14}$, $R^{15}$, $R^{21}$, $R^{22}$, $R^{23}$, $R^{24}$ and $R^{25}$ represents a group having a chainlike structure of which the number of the atoms of the main chain is from 4 to 20, and the remaining ones each independently represent a hydrogen atom or a substituent.

13. The method for producing an organic semiconductor device according to claim 11, wherein the solution is a solution in a halogen solvent.

14. The method for producing an organic semiconductor device according to claim 11, wherein the solvent is an aromatic solvent.

15. A compound having a structure represented by the following formula (2) from a solution of the compound:

(2)

wherein $X^1$, $X^2$ and $X^3$ each independently represent an oxygen atom, a sulfur atom, a selenium atom or a tellurium atom; $R^1$ and $R^3$ each independently represent a hydrogen atom or a substituent; at least one of $R^{11}$, $R^{12}$, $R^{13}$, $R^{14}$, $R^{15}$, $R^{21}$, $R^{22}$, $R^{23}$, $R^{24}$ and $R^{25}$ represents a group having a chainlike structure of which the number of the atoms of the main chain is from 4 to 20, and the remaining ones each independently represent a hydrogen atom or a substituent.

16. A compound according to claim 15, wherein the group having a chainlike structure in which the number of the carbon atoms constituting the main chain is from 4 to 20 has a structure represented by the following formula (5):

(5)

wherein Ar represents an aromatic linking group; and m indicates an integer of from 4 to 20.

17. The compound according to claim 15, wherein the group having a chainlike structure in which the number of the carbon atoms constituting the main chain is from 4 to 20 has a structure represented by the following formula (6):

(6)

wherein Ar represents an aromatic linking group; and m indicates an integer of from 4 to 20.

18. The compound according to claim 15, wherein at least one of $R^{13}$ and $R^{23}$ is a group having a chainlike structure in which the number of the carbon atoms constituting the main chain is from 4 to 20.

19. The compound according to claim 15, wherein at least one of $R^{13}$ and $R^{23}$ is a group having a chainlike structure in which the number of the carbon atoms constituting the main chain is from 8 to 20.

20. The compound according to claim 15, wherein $X^1$, $X^2$ and $X^3$ are the same atoms.

21. The compound according to claim 20, wherein $X^1$, $X^2$ and $X^3$ are sulfur atoms.

22. The compound according to claim 15, wherein $X^1$ and $X^3$ are sulfur atoms and $X^2$ is a selenium atom or a tellurium atom.

23. An organic semiconductor device comprising the compound of claim 15.

* * * * *